United States Patent [19]

Clyde

[11] Patent Number: 5,256,570
[45] Date of Patent: Oct. 26, 1993

[54] BIOREACTOR CONFIGURED FOR VARIOUS PERMEABLE CELL SUPPORTS AND CULTURE MEDIA

[76] Inventor: Robert A. Clyde, P.O. Box 740644, New Orleans, La. 70174

[21] Appl. No.: 964,071

[22] Filed: Oct. 20, 1992

[51] Int. Cl.$^5$ ............................................. C12M 3/04
[52] U.S. Cl. .................... 435/285; 435/312; 435/313; 435/813; 210/619; 210/150
[58] Field of Search .............. 435/284–287, 435/288, 299, 300, 310, 311, 312, 313, 315, 316, 813; 422/184, 209; 210/615, 619, 150, 151

[56] References Cited

U.S. PATENT DOCUMENTS

| | | | |
|---|---|---|---|
| 3,389,798 | 6/1968 | Hartman et al. | 210/150 |
| 3,594,277 | 7/1971 | Mako et al. | |
| 3,847,811 | 11/1974 | Stengelin | 210/150 |
| 4,431,537 | 2/1984 | Hirota | 210/150 |
| 4,446,236 | 5/1984 | Clyde | 435/312 |
| 4,468,326 | 8/1984 | Kawert | 210/619 |
| 4,532,035 | 7/1985 | Fuchs et al. | 210/150 |
| 4,537,678 | 8/1985 | Thissen | 210/150 |
| 4,540,491 | 9/1985 | Zimmer | 210/619 |
| 4,554,075 | 11/1985 | Chang et al. | 210/619 |
| 4,600,694 | 7/1986 | Clyde | 435/312 |
| 4,655,926 | 4/1987 | Chang et al. | 210/619 |
| 4,877,731 | 10/1989 | Ling et al. | |
| 4,963,486 | 10/1990 | Hang | |
| 4,999,302 | 3/1991 | Kahler et al. | 210/619 |

FOREIGN PATENT DOCUMENTS

| | | | |
|---|---|---|---|
| 1008191 | 4/1977 | Canada | 210/619 |
| 0008810 | 3/1980 | European Pat. Off. | 210/150 |
| 8700199 | 1/1987 | PCT Int'l Appl. | 435/288 |
| 1581832 | 12/1980 | United Kingdom | 435/310 |

OTHER PUBLICATIONS

Miller et al., "Effects of Dissolved Oxygen Concentration on Hybridoma Growth and Metabolism in Continuous Culture". Journal of Cellular Physiology, vol. 132 (1987) pp. 524–530.

Spiker et al. "Influence of 2,4,6-Trinitrotoluene (TNT) Concentration on the Degradation of TNT in Explosive-Contaminated Soils..." Applied and Environmental Microbiology (Sep. 1992) pp. 3199–3202.

Tiwaree et al. "Biological Deodorization of Dimethyl Sulfide Using Different Fabrics as the Carriers of the Microorganisms". Applied Biochem. and Biotech. vol. 32 (1992) pp. 135–148.

Chiou et al. "A Fiber-Bed Bioreactor..." Biotech & Bioeng. vol. 37 (1991) pp. 755–761.

Facchini et al. "Plant Cell Bioreactor..." Biotech. & Bioeng. vol. 37 (1991) pp. 397–403.

Miller et al. Journal of Cellular Phys. vol. 132 (1987) p. 524.

Oller et al. Journal Cell Sci. vol. 94 (1989) pp. 43–49.

Sakurai et al. Journal of Ferment. vol. 73 (1992). pp. 251–254.

Webb et al. Plant and Animal Cells. Holstead Press-J. Wiley (New York (1987) pp. 94–99.

Primary Examiner—Michael G. Wityshyn
Assistant Examiner—William H. Beisner
Attorney, Agent, or Firm—Joseph T. Regard

[57] ABSTRACT

A design for a RBC (rotary biological contactor), wherein there is provided a plurality of support members enveloped in a chamber, configured so as to support microorganisms or cells. Specifically, the support members are corrugated sheet media which include drain holes formed therein. The corrugated sheet media are supported within a rotating infusion unit which is positioned so as to rotate within an outer jacket. The RBC also includes a system to vary the nutrient environment of said microorganisms or cells, including means to vary the temperature and/or atmosphere within the jacket and infusion unit.

5 Claims, 3 Drawing Sheets

BIOREACTOR CONFIGURED FOR VARIOUS PERMEABLE CELL SUPPORTS AND CULTURE MEDIA

BACKGROUND OF THE INVENTION

1. Invention Field

The present invention teaches various designs for bioreactors, including an RBC (rotary biological contactor) wherein there is provided, in the preferred embodiment of the present invention, a plurality of barrier members enveloped in a chamber, configured to provide a plurality of nutrient chambers for microorganisms or cells.

The preferred embodiment teaches a plurality of disk configured, rotating chamber partition members, enveloped by a generally horizontally situated, cylindrical chamber member, and wherein there may be further included a system to vary the nutrient environment of said micro-organisms or cells, including means to individually vary the temperature and/or atmosphere of each of said chamber areas.

Alternative embodiments of the present invention teach the utilization of various permeable cellular support media in facilitating an optimal system for retaining and nurturing various micro-organisms or cells, coupled with a rotating or rolling RBC or Bioreactor.

2. General Background Discussion

Several types of cells, especially fungi, plant and mammalian cells, require oxygen for growth and sustenance. Many antibiotics, including such organisms as penicillin and streptomycin, also require oxygen. In addition, various strains of living tissues and organisms have been found to metabolize and break down various toxic and/or heretofore environmentally undisposable materials.

For example, the fungus *Phanerochaete chrysosporium* (white rot) has been found to degrade TNT (trinitrotoluene) as well as chlorine compounds in pulp mill effluent. The fungus *Rhizopus arrhizus* is able to leach out toxic metals, while *Rhizopus oryzae* makes lactic acid for biodegradable polymers. The fungus *Aspergillus niger* is able to synthesize citric acid and food flavors. Mammalian cells have been known to produce interferon. Plant cells produce alkaloids.

The advantages of plug flow are well known to engineers, in accelerating the metabolism of these various materials by the living tissues, due in part to plug flows suitability for providing continuous reactions. With plug flow, product inhibition is low in the first section, but this is not true when back mixing takes place. In an effort to provide plug flow in an RBC (rotary biological contactor) with solid plastic discs, baffles are employed, but these are not very effective because liquid can go around the baffle and by-pass the discs. The prior art has yet to contemplate an RBC configured to provide better plug flow. Even further, the prior art has not contemplated a bioreactor which may be utilized in conjunction with a variety of permeable cell supports or various culture media, prior art designs being largely limited to specific applications with little diversity.

While the generalized concept of the RBC has been well contemplated in the prior art, what is needed is an improved reactor wherein the operating efficiency and growth viability, and versatility, is substantially enhanced.

U.S. Pat. No. 4,655,926 by Chang et al contemplates a rectangular tank with rotating solid plastic discs for retaining the cell cultures in several chamber sections, further teaching oxygen fed into one end of the tank, run in a batchwise fashion. This is as opposed to a continuous flow system, which requires less labor and is more efficient, avoiding product inhibition near the end of the run. When running continuously, feeding oxygen on one end, product inhibition is low in the first section. Further, with solid plastic discs, cells grow only on the outside of the disc. On the other hand, if the discs were comprised of a permeable material, such as polyurethane foam, cells would grow on the inside of the disc also.

Instead of having straight sides of the tank, when the tank is curved, just slightly larger diameter than the discs and run half full, liquid and oxygen feed is forced through the permeable discs and better contact is made and no foaming is experienced. Accordingly, liquid permeates the bottom half of the discs, while the gas permeates the top portion.

With the prior art solid plastic discs, cells are found only on the outside of the disc, limiting the habitable area by two dimensions. This is as opposed to a three dimensional disc system, wherein significantly more cells could be employed. Solid plastic, like stainless, is hard, completely impermeable to fluid medium, and is not conducive to cell growth, as opposed to a "soft" surface.

A list of prior patents which may be of interest is presented below:

| U.S. Pat. No. | Patentee(s) | Issue Date |
| --- | --- | --- |
| 3,594,277 | Mako | 07/20/1971 |
| 4,468,326 | Kawert | 08/28/1984 |
| 4,554,075 | Chang et al | 11/19/1985 |
| 4,655,926 | Chang et al | 03/07/1987 |
| 4,877,731 | Ling et al | 10/31/1989 |
| 4,963,486 | Hang | 10/16/1990 |
| 4,999,302 | Kahler et al | 03/12/1991 |

Publications which may be of interest may include:

Miller, W., Wilke, C., and Blanch, H.: Effects of Dissolved Oxygen Concentration on Hybridoma Growth and Metabolism in Continuous Culture. Jour Cellular Phys 132:524–530 (1987).

Webb, C. and Mavituna, F.: Immobilization of Plant Cells in a Reticulated Foam Matrix. Plant and Animal Cells, Holstead Press - J. Wiley (New York) 94–99.

Oller, A., Buser, C., Tyo, M., and Thilly, W.: Growth of mammalian cells at high oxygen concentrations. Jour Cell Sci 94, 43–49 (1989).

Facchini, P., and DiCosmo, F.: Plant Cell Bioreactor for the Production of Protoberberine Alkaloids from Immobilized *Thalictrum rugosum* Cultures. Biotech and Bioeng 37, 397–403 (1991).

Chiou, T., Murakami, S., Wang, D., and Wu, W.: A Fiber-Bed Bioreactor for Anchorage-Dependent Animal Cell Cultures: Part I. Bioreactor Design and Operations. Biotech and Bioeng 37, 755–761 (1991).

Sakurai, A. and Hiroshi, I.: Effect of Operational Conditions on the Rate of Citric Acid Production by Rotating Disc Contactor Using *Aspergillus niger*. Jour Ferm and Bioeng. Vol 73, 3, 251–254 (1992).

Tiwaree, R., Cho, K., Hirai, M. and Shoda, M.: Biological Deodorization of Dimethyl Sulfide Using Different Fabrics as the Carriers of the Microorganisms. Applied Biochem and Biotech 32, 135–148 (1992).

NSW Corporation: Biofilter Media, RBCs and Tower Packings. Sales Brochure.

Heidman, J. A., Brenner, R. C., and Gilbert, W. G.: Summary of Design Information On Rotating Biological Contactors. EPA-430/9-84-008.

U.S. Pat. No. 4,554,075 to Chang is similar to '926 above. In col 3, line 9, it is stated that said system can operate in a plug flow mode, however, "plug flow" by definition means no back mixing will occur, and there is back mixing in the taught apparatus, in the first compartment, when liquid enters the first compartment it can by-pass the first disc and go to the second disc.

U.S. Pat. No. 4,468,326 to Kawert teaches a system (col 2 line 19) wherein he says baffles are arranged so as to prevent water from shunting past the rotors. However, with thin discs, media could by pass discs when baffles (7) are far apart as in FIG. 1b. Curved tank sides close to the discs would prevent by-pass. When the sides of the tank are curved and close to the disc, baffles are not required.

Iyer gave talk 100 BIOT at the American Chemical Society Meeting in San Francisco in April, 1992, wherein he disclosed his ability to produce lactic acid with the fungus *Rhizopus oryzae* or *arrhizus*, utilizing an RBC having solid plastic discs.

Hang, in U.S. Pat. No. 4,963,486 also has a process for making lactic acid with this fungus. Lactic acid polymers are biodegradable, so this should reduce landfills, which are piling up. Ling, in U.S. Pat. No. 4,877,731, describes such a process.

Conventional methods of adding oxygen involve bubbling the gas up from the bottom of the RBC, through the liquid medium. However, the solubility of the gas in water is only about 10 ppm. There is a stagnant region around the bubble, then it has to go through the bulk liquid, another stagnant region around the cell and then through the cell wall for the oxygen to get to the cell. This is shown in the publication *Biochem Eng Fundamentals* (2nd ed), Baily and Ollis (McGraw Hill) p. 460.

Immobilization of the plant cells in reticulated foam depends upon the size of the cell, as far as picking the size of the pores. In the publication *Plant and Animal Cells*, Webb and Mavituna (John Wiley) Ch 6 illustrates the depth of entrapment in 10 pores per inch, 30 ppi and 40 ppi (pg 97). They also describe a method of getting smaller cells by homogenization (p 98). It would be desirable to have larger pore sizes near the entrance of the reactor, and smaller pores near the exit, in order to entrap the largest number of cells, while allowing for gas permeability. One such method, uncontemplated in the prior art, could entail the combining of foam and rice hulls.

Rice hulls contain cellulose, hemicellulose, silica (about 20-23%) and other metals needed for growing *Phanerochaete chrysosporium*. Soybean hulls contain about 8% protein. Cellulose has adjacent glucose fragments linked in a 1,4 beta linkage, whereas starches are 1,4 alpha linkage and are easier to break down, but *Phanerochaete chrysosporium* has cellulase enzymes, so if a little water is added, it can break down cellulose, but if the hulls are coated with a little starch-glucose, it reacts faster.

Instead of oxygen, odor causing gasses such as dimethyl sulfide and hydrogen sulfide can be removed with organisms on fabrics, as described in the above referenced article entitled "Biological deodorization of dimethyl sulfide ... " in Applied Biochem and Biotech. These are the very gasses emitted by paper mills.

Formaldehyde gas is found in morgues and factories using urea formaldehyde resins. It is soluble in water, and Professor Moyer of the Biology Department at Trinity University has found an organism, which he has grown on polyester fiber, that degrades it.

Plant and mammalian cells also require oxygen. Many of these cells are fragile (sheer sensitive) and when oxygen is bubbled up from the bottom of a conventional fermenter, large air compressors are needed and the bubbles burst at the surface, causing foam and damage to the cells. To avoid this, Wang et al, in Biotech and Bioeng 37, 755-76 with a vertical reactor (not an RBC), put air up the lower middle portion of the containment vessel, with the liquid configured to overflow around the outside of the partitions, flowing down through fiberglass. M. Lavery, and A. W. Nienow infused silicone antifoam (6 ppm) to reduce the $K_La$ value by ca.50% in their paper *Oxygen Transfer in Animal Cell Culture Medium* Biotech and Bioeng, Vol XXX, P 368-373 (1987). CHO (chinese hamster ovary) cells produce interferon. Wang says that this design could be scaled up (p 756), but their unit was only 35 cm high, and if it were much higher, the oxygen would be depleted as it reached the bottom.

Wang further asserts (p 760) that the "top layers had more cells than the bottom layers". Chang ('926 reference) asserts that oxygen concentration is important (col 4 line 37). Facchini says (p 402) more cells near the perimeter.

In the design of the present, applied for invention, oxygen distribution is configured such that concentration is uniform throughout the various partitions, with almost the same concentration from end to end, but if the support causes some pressure drop, more oxygen can be put in the top of the middle section 103, as shown in FIG. 1. As solubility of the gas in water is relatively very low, direct contact is better.

When the gas is pressurized in the headspace above the liquid, even better solubility is obtained. Plant cells also produce valuable alkaloids. Facchini and DiCosmo, Biot and Bioeng 37, 397-403 produced alkaloids on glass fiber, but it took several days. With a more efficient reactor, the time could be shortened. There were more cells near the perimeter (pg 402) since air reached them better.

Heidmann, Brenner, and Gilbert summarize the state of the art in RBC's in their treatise *Summary of Design Information on Rotating Biological Contactors* (EPA 1984):

"Each manufacturer designs its own shape, size, and thickness of shaft, the wall thickness of the shaft is governed by structural requirements, and the shape is highly dependent on the method the manufacturer employ in supporting the plastic media from the shaft. The five manufacturers each utilize a shaft that differs from the others in either the thickness, size, or shape, or in some cases all three. Structurally, these differences are readily apparent as shown in FIG. 2 and identified in Table One.

MEDIA

The heart of the RBC process is the plastic media. In 1972, the high density polyethylene (HDPE) disc was introduced as a cost reduction alternative the previously used 0.5 inch thick polystyrene disc. The major advantage of polyethylene is its ability to be formed into various configurations that require a thickness of only 40 to 60 mils (0.04 to 0.06 in.). This innovation enabled 100,000 to 180,000 square feet of surface area to be provided on a 27 foot shaft with 12 foot diameter media. Today, all U.S. manufacturers of RBC's utilize polyethylene as their plastic media.

SECTION 2
PROCESS DESCRIPTION

All RBC systems are cylindrical-type structures consisting of plastic media attached to and/or supported by horizontal rotating shafts. The first commercial RBC system was installed in West Germany in 1960. Units constructed from this time to the early 1970's used flat 0.5 inch thick, 6.5-10 foot diameter expanded polystyrene disks. All present systems use thin (0.04 to 0.06 in) high density plastic media either formed as discs or sections of discs and aligned perpendicular to the shaft, or spirally wound onto and aligned parallel to the shaft."

Thus, the prior art RBC's have been of largely limited structure and usage, its limitations to large extent brought about due to the relatively impermiable, two dimensional solid cell supports, as opposed to a three dimensional, fluid and cell permiable support, as is contemplated in the present, applied for invention.

BRIEF DESCRIPTION OF THE INVENTION

Although the prior art apparently contemplates in great part the utilization of HDPE and similar solid plastic media, there are several types of permeable cell supports, including Polyurethane foam, rice hulls inside a screen, fiber sheets with holes, or polyester or glass fiber with randomly oriented threads. The polyester is sometimes called "fiberfill" and used to stuff pillows, sleeping bags and the like. For more surface area, CELITE® processed diatom skeleton material, distributed by Manville Products Corporation of Denver, Colo. can be entrapped in fiber which might be utilized with much greater effect than the prior art.

In operation, it is better to sterilize the reactor until a good growth is obtained. Many of the supports may be autoclaved at 120° C.

A Petri dish of *Phanerochaete chrysosporium* was obtained from Prof. Bayman at Tulane University, and this fungus grew on all of said supports. By coating the supports with a starch-sugar solution, the fungus grew faster. This fungus degrades and decolorizes pulp mill effluent and TNT, and when coated on rice hulls, old newspapers, wood chips, sawdust, corn cobs, or polyurethane foam, it could be plowed into contaminated soil, breaking down the contaminants in an environmentally sound fashion. With billions of pounds of rice hulls available at a very low cost, this could be a very attractive means of decontaminating waste dumps and the like.

Corrugations, such as box material, have been found to entrap air, so the fungus grows better. Rice hulls, sawdust, etc. can be entrapped in the corrugations. Some cardboard boxes can withstand 200 lbs pressure, so they will maintain their shape even with dirt on top.

It is therefore an object of the present invention to provide a cost effective, highly efficient system for supporting a variety of culture media utilizing various permeable and non-permeable cell supports.

It is another object of the present invention to provide a new and innovative, three dimensional cellular support media in a bioreactor system.

It is another object of the present invention to provide a bioreactor configured for providing optimal oxygen or other gas infusion, depending upon the culture media present.

It is still another object of the present invention to provide a bioreactor configured specifically for containing granular support media.

Lastly, it is an object of the present invention to provide a bioreactor configured to sustain *Phanerochaete chrysoporium* in a moving, three dimensional culture media.

BRIEF DESCRIPTION of the DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE INVENTION

Figure 1:
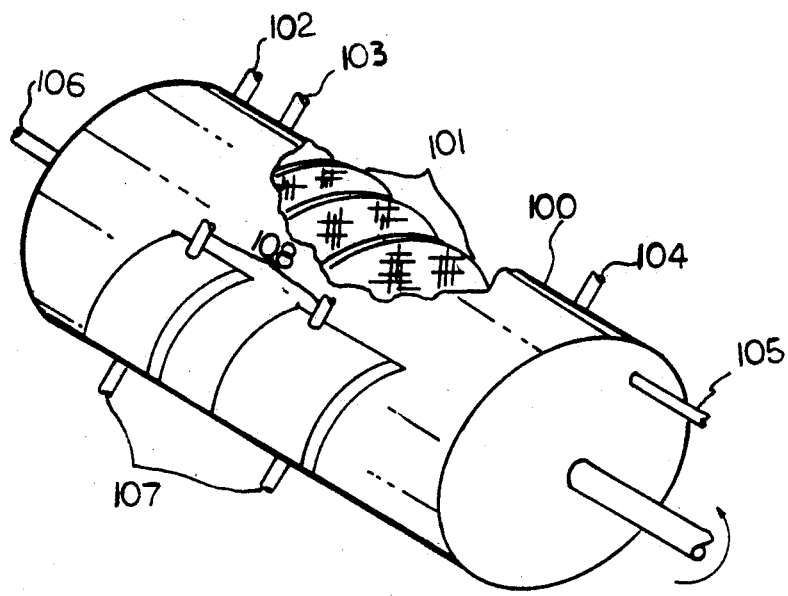
FIG. 1 is an isometric view of the preferred embodiment of the present invention, wherein there is provided an array of rotating discs of fiber or polyurethane.

As can be seen in FIG. 1, the reactor 100 of the preferred, exemplary embodiment of the present invention, includes a plurality of rotating discs 101 of fiber or polyurethane. Oxygen or other gas is infused at nozzle 102, and if it is a long unit at 103 and out at 104. Liquid for temperature control is put into jacket at 107 and out at 108. It is understood that other openings for temperature, dissolved oxygen, and pH are also required. By putting liquid and gas countercurrent, there is less product inhibition, as the organisms receiving the greater concentration of oxygen are better able to metabolize the liquid at the latter stage of plug flow, where the liquid needs more oxygen to complete the reaction, due to the depletion of the consumed media in the liquid. With polyurethane foam discs, discs having formed therein larger openings (such as 10 pores per inch) are put near the liquid inlet and smaller openings (such as 40 ppi) at the other end.

Figure 2:
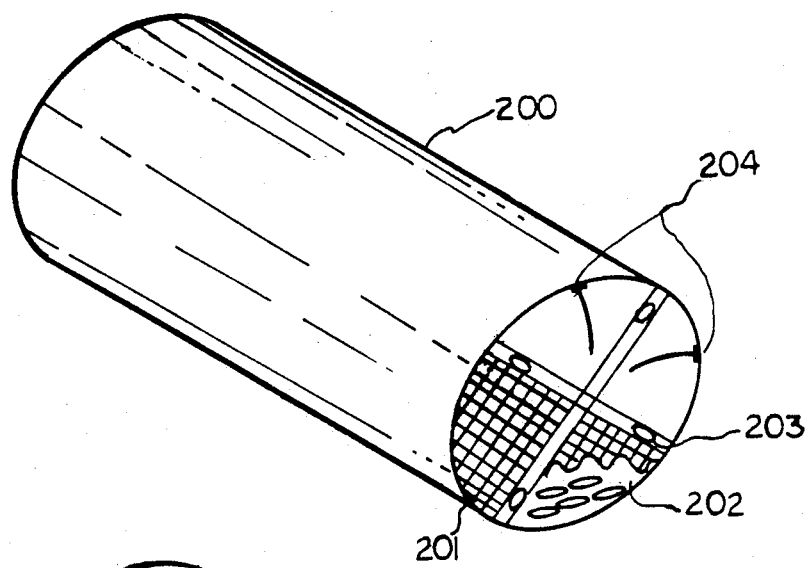
FIG. 2 is an isometric view of an alternative embodiment of the invention of FIG. 1, wherein there is provided a system for containing granular materials in lieu of the disc array.

FIG. 2 illustrates an alternative embodiment of the present invention, wherein there is provided as an alternative to the discs 101, an infusion rotation unit 200 configured to contain granular items 202, such as rice hulls, peanut hulls, soybean hulls, wood chips, corn cobs, or similar material. 201 is a screen. Holes 203 in the cross braces allow the circulating fluid to pass therethrough, while allowing the braces to lift the liquid during operation. Fins 204 are provided to urge the granular material to circulate with the rotation of unit 200, enhancing oxygenation with the gas flow.

Figure 3:
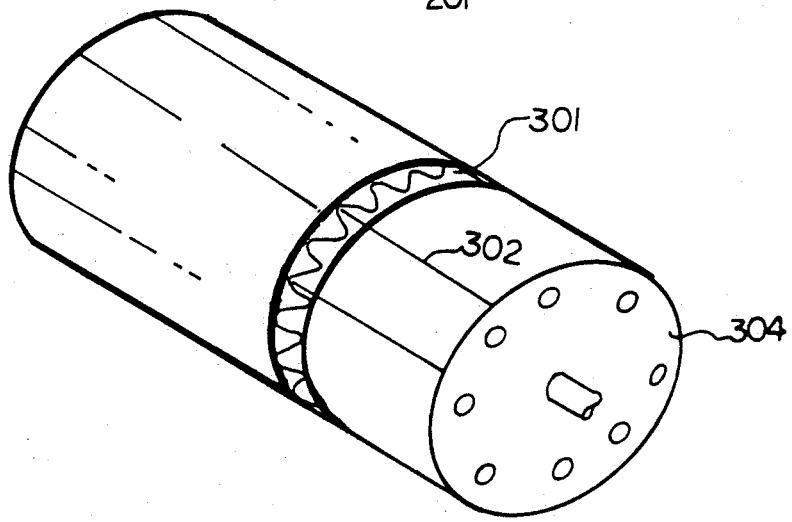
FIG. 3 is an isometric view of an alternative embodiment of the invention of FIG. 1, wherein there is provided a corrugated material in lieu of the disc array.

FIG. 3 illustrates still another alternative embodiment of the present invention, wherein there is provided still another infusion rotation unit 301, configured to contain corrugated fiber, such as cellulose cardboard or the like. Wires 302 help support the corrugations and holes in the corrugations. Said wires are attached to an end plate 304, and another end plate (not shown) at the other end. These wires can also support randomly oriented fibers or polyurethane foam.

If foam is used with liquid containing solids, such as homogenized plant cells, foam discs having larger openings are placed nearest the first end of the rotation unit. Corrugations with *Phanerochaete chrysosporium* can degrade chlorine compounds in the reactor or buried in soil so air is entrapped. Corrugated plastic can also be obtained from companies that make containers for cakes or salad bars. The wires can also support randomly oriented polyester or glass fibers.

Figure 4:
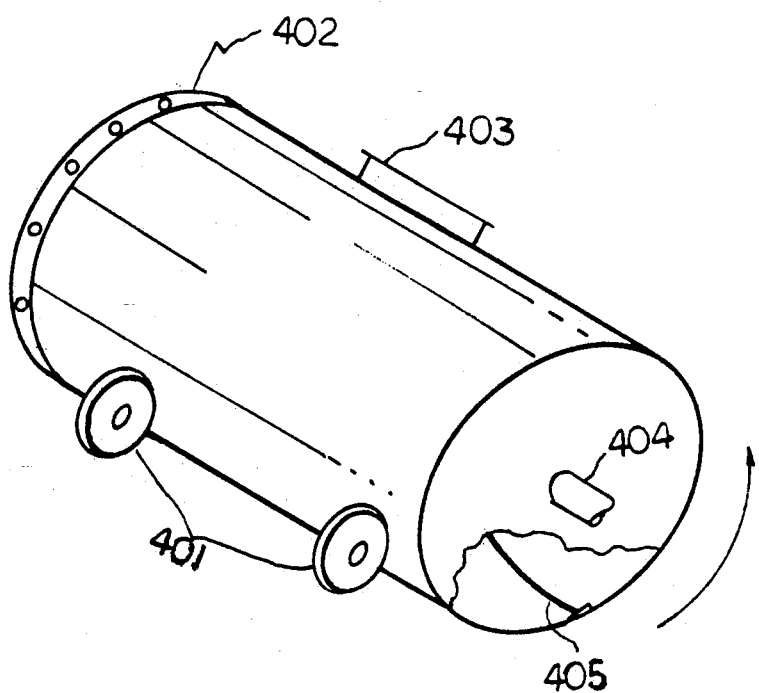
FIG. 4 is an isometric view of an alternative embodiment of the invention of FIG. 1, wherein there is taught a system for rotating the entire tank unit, configured to encompass granular material.

FIG. 4 shows still another embodiment wherein the entire tank rotates from wheel supports/rollers 401 which are turned by a motor (not shown). Rice hulls or other material is put in through manhole 403 or flange 402. Liquid is put in (and $O_2$ gas out) through nozzle 404 as further shown in FIG. 9, wherein a tight fitting rubber hose 901 is provided that is configured to slip relative to the tank, since the tank is turning and the inlet pipe is not. As shown, liquid is put in the bottom half and gas at the top. Returning to FIG. 4, $O_2$ is put in (and liquid out) a nozzle in the middle of the far end of the tank. Temperature is controlled by spraying water outside the tank. A similar opening is in the middle of the far end (not shown) to put gas in and liquid out. Tank is filled with rice hulls or similar material. In addition to rice hulls, the present embodiment can also accept and treat ground telephone poles or the like contaminated with PCP (penta chlorophenol). Fins 405 are provided to urge the granular material to circulate with the rotation of unit 200, enhancing oxygenation with the gas flow.

Figure 9:
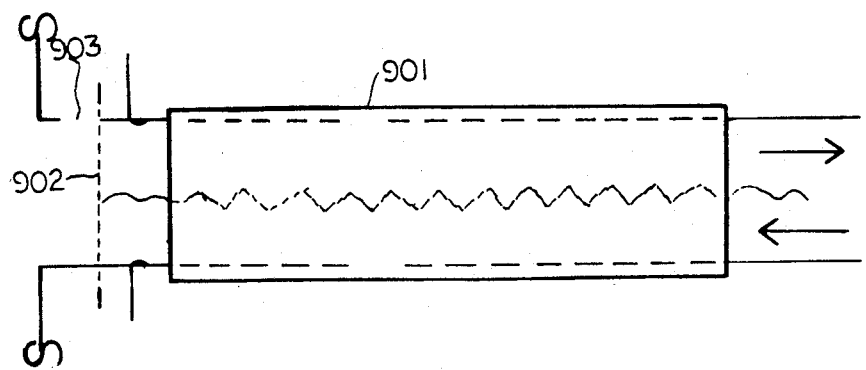
FIG. 9 is a side, partially cut-away view illustrating the migration of liquids and gasses through the apparatus of the present invention.

Referring to FIG. 9, a screen 902 may be utilized with the present apparatus to keep the rice hulls in the tank of FIG. 4, and may also include a hatch or service aperture 903 to clean the screen. It is noted that the screen is especially important on the far end of the reactor, where the liquid flows out, as this area may tend to clog, depending upon the type of media involved.

Figure 5:
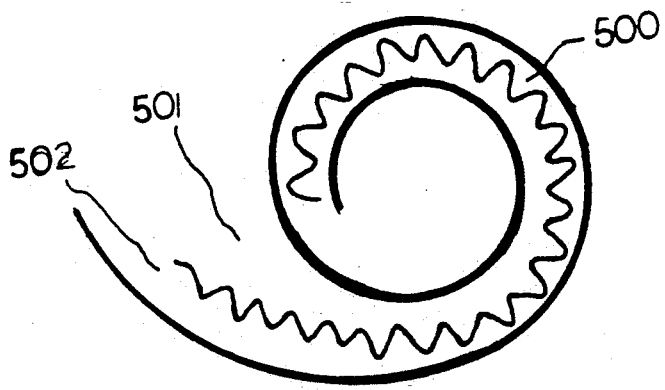
FIG. 5 is a side view of the invention of FIG. 3, wherein there is illustrated the arrangement of the corrugated material within the system.

FIG. 5 illustrates corrugations 500 (301 in FIG. 3) wrapped around core. Rice hulls or similar material can be put in at 501 and 502 such that they are on both sides of the corrugations.

Figure 6:
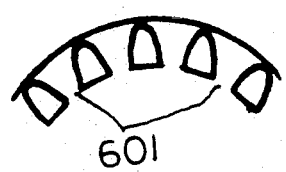
FIG. 6 is a side, partial view of the invention of FIG. 5, wherein there is illustrated the forming of apertures of the corrugation arrangement of FIG. 5.

FIG. 6 shows the corrugations as in FIG. 5, wherein holes 601 may be punched in the trough such that water drips down, allowing for greater mass transfer via droplets, as opposed to a flat surface.

Figure 7:
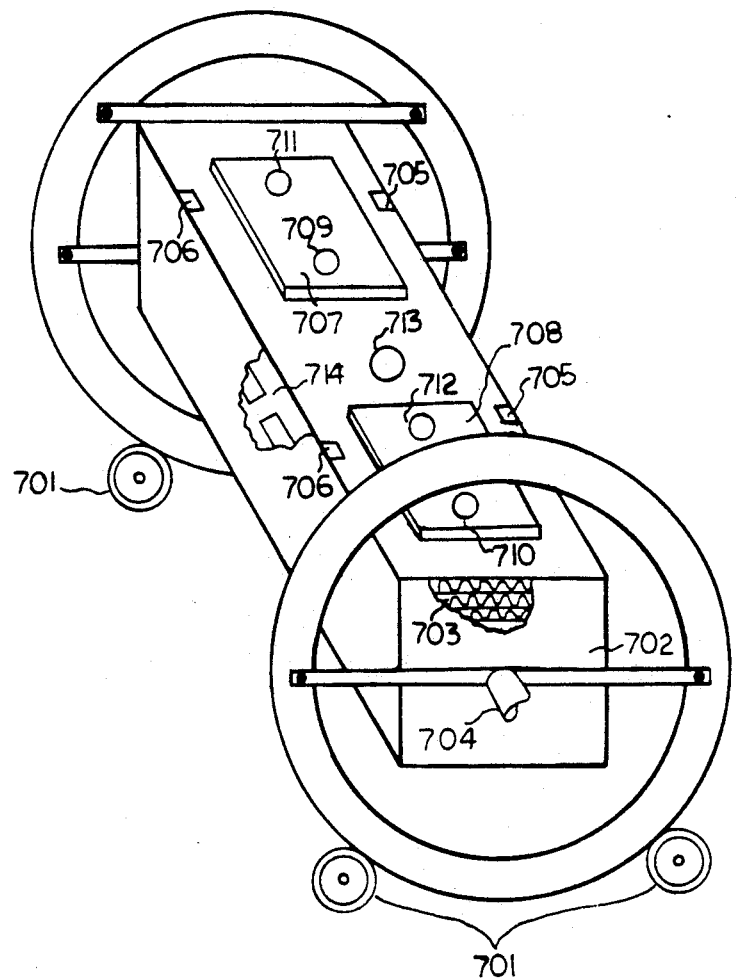
FIG. 7 is a top, isometric view of an alternative embodiment of the invention of FIG. 1, wherein there is contemplated a device for providing a rolling motion in back and forth fashion, as opposed the rotation contemplated in FIG. 1.

FIG. 7 illustrates a unit wherein the entire container component 702 is rocked back and forth via rollers 701. Then, every 15 minutes or so, it rotates 180°, and the oxygen is put in the nozzle, which was formerly on the bottom, and oxygen is shut off to the nozzle, which is now on the bottom. Then, in 15 minutes, it rotates 180° again, but in the opposite direction, so that the flexible hoses to the jackets and oxygen do not become entangled.

Liquid is put in at nozzle 704 and out the far end. Oxygen is put in at the far end, and also at 713 and out at 704. Nozzle 704 is in the middle so it turns, but stays in the same place as the unit turns 180°.

Inside component 702 are layers of acrylic plastic 703, or PLEXIGLAS TM. The present components have grooves about 3/16 inch apart so liquid and gas can pass through. As an alternative, other types of plastic or rubber may be utilized with similar satisfactory results. Liquid is put in (and gas out) at 704. The other end has an opening in the middle for gas inlet and a liquid outlet. Newspapers or other material can be put between the sheets 703. Hinge 705 enables the top to be opened and bolt 706 holds it down. Jackets 707, 708 for temperature control are provided on the top and same on the bottom. In this exemplary embodiment, liquid flow is implemented through said jackets 707, 708 for varying the temperature as desired via thermostatic or manual controls.

Inlets 709, 710 and outlets 711, 712 are provided with component 702. Oxygen is put in at 713 through a gap in the supports 714. A similar oxygen entry is on the bottom.

Figure 8:
FIG. 8 is a side, cross-sectional view of stacked, ribbed cloth, which may be utilized as an alternative medium in the present invention.

Cloth, having ribs, as shown in FIG. 8, has been found to be ideal for the growth of white rot fungus thereon. Item 801 is cloth and 802 is plastic. Some plastics cannot be autoclaved, but there are other ways to sterilize.

In operation, as shown in FIG. 1, the unit is put in semisterile condition and inoculated with the fungus *Phanerochaete chrysosporium*, then put in a secondary metabolic state as is well known by those skilled in the art, as described in Chang's U.S. Pat. No. 4,655,926.

Tests have shown that organism detachment occurs at a certain definite rate of movement. A test suitable for use in the present invention to evaluate the adhesion between a selected organism and a selected fiber webbing consists of pumping the organism cells up through an orifice and then radially across a plate to which the fiber webbing is attached. At a particular pumping rate the sheer forces are too great and the organism becomes detached from the webbing. The optimum rate of relative motion between the liquid solution and the webbing must then be slightly less than the above-noted rate. A device for measuring organism adhesion is commercially available from Dr. Fowler of the Chemical Engineering Department at the University College of Swanesa in England, or from an associated company. This device can be used to check the adhesion, as the different cells have different adhesion properties, so the rate of adhesion for the appropriate cells is determinable by utilizing this device.

To grow white rot fungus, the unit is put into a sterile or semi sterile state. Medium consists of $KH_2PO_4$, $MgSO_4$, $CaCl_2$, $NH_4Cl$, thiamine and glucose. Instead of glucose, inexpensive corn syrup can be used, then after about two days, the nitrogen is consumed and the fungus enters a secondary metabolic state, and is able to decolorize pulp mill effluent. Persons skilled in the art know this, and it is described in Chang's patent 4,655,926 and also in the J. of Bacteriology, September 1978, Pages 790-797. The addition of a small amount of detergent such as Tween 80 TM has beneficial effect. But the most important thing is to supply a high amount of oxygen, as Chang says in Col 4, Line 40. By putting the fungus on corrugations and burying in soil so air is entrapped is not covered in previous patents. *Phanerochaete sordida* can be grown in similar fashion, and may have some advantages over chrysosporium.

To grow *Rhizopus oryzae*, the unit is also put in a sterile or semi-sterile state. Inexpensive potato waste can be used in the media, together with a little glucose. Lactic acid can be recovered with a resin, as known by those skilled in the art. Optimum temperature is about 24° C. Inexpensive urea is a nitrogen source.

*Aspergillus niger*. Sterile or semi sterile state. Media is sucrose, $KH_2PO_4$, $NH_4NO_3$, $MgSO_4$, $MnSO_4$, and $FeCl_3$, and Temperature 30°.

*Rhizopus arrhizus* is similar to *Rhizopus oryzae*. After growing on the unit, it can remove uranium and thorium as known by those skilled in the art, especially professor B. Volesky at McGill University in Montreal.

To grow Chinese hamster ovarian cells, the medium is Dulbecco's modified Eagle's medium, supplemented with fetal bovine serum, glutamine, methotrexate, and antibiotics as described by Wang et al in Biot and Bioeng. Vol. 37, Page 757, which reference is incorporated in the present specification in its entirety. It is not necessary to use an antifoam, however, because oxygen is supplied from the headspace. Some $CO_2$ may also be necessary, about 5%.

Growth of plant cells is well known to those skilled in the art. They can be given a short homogenization and then grown on foam, with larger foam opening first followed by smaller openings.

EXAMPLE 1

Several pieces, including corrugated fiber cloth 292540 from Cloth World TM, rice hulls, Reemay TM polyester, polyurethane foam, randomly oriented polyester, and brown corrugations from the Stone Container Company TM of New Orleans, were put in a horizontal tube, sterilized, rotated, and inoculated with *Phanerochaete chrysosporium*. In a few days, white growth was observed on all. Some distilled water was added prior to sterilization. The oxygen in the tube was enough for this small unit, but for larger units, more $O_2$ is required.

EXAMPLE 2

The experiment was repeated with stainless mesh and solid polyethylene. No growth was observed.

In still another alternative embodiment of the present invention, the plug flow system can be configured to re-circulate liquid back into the reactor until the liquid has been processed to the desired level.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A bioreactor configured for various permeable cell supports and culture media, comprising:
   a jacket having first and second ends, said jacket configured to form a somewhat cylindrical interior, said interior having an internal diameter;
   liquid infusion means for infusing liquid into said jacket;
   oxygen infusion means for infusing oxygen into said jacket;
   a generally cylindrically configured infusion rotation unit containing a corrugated sheet media having drain holes formed therein, said infusion rotation unit having an outer diameter slightly less than the internal diameter of said jacket, said infusion rotation unit further including support means to support said corrugated sheet media in place.

2. The bioreactor of claim 1, wherein said corrugated sheet media is spirally wound.

3. A bioreactor configured for various permeable cell supports and culture media, comprising:
   a jacket having first and second ends, said jacket configured to form a somewhat cylindrical interior, said interior having an internal diameter;
   liquid infusion means for infusing liquid into said jacket;
   oxygen infusion means for infusing oxygen into said jacket;
   a generally cylindrically configured infusion rotation unit containing corrugated sheet media, said infusion rotation unit having an outer diameter slightly less than the internal diameter of said jacket, said corrugated sheet media having drain holes formed therein and being spirally wound.

4. The bioreactor of claim 3, wherein said corrugated sheet media has disposed therein diatom skeleton material.

5. The bioreactor of claim 3, wherein said corrugated sheet media is comprised of a randomly oriented fiber sheet.

* * * * *